United States Patent [19]

Kapp et al.

[11] 4,196,203
[45] Apr. 1, 1980

[54] NOVEL CORTICOIDS

[75] Inventors: Joachim-Friedrich Kapp; Klaus Kieslich; Henry Laurent; Karl Petzoldt, all of Berlin, Fed. Rep. of Germany

[73] Assignee: Schering Aktiengesellschaft, Bergkamen & Berlin, Fed. Rep. of Germany

[21] Appl. No.: 858,975

[22] Filed: Dec. 9, 1977

[30] Foreign Application Priority Data

Dec. 10, 1976 [DE] Fed. Rep. of Germany ....... 2656575
Nov. 30, 1977 [DE] Fed. Rep. of Germany ....... 2753839

[51] Int. Cl.$^2$ ............... A61K 31/56; C07J 5/00
[52] U.S. Cl. ............... 424/242; 260/397.45; 260/239.55 R; 260/397.47; 435/54
[58] Field of Search ............ 260/397.45; 424/242

[56] References Cited

U.S. PATENT DOCUMENTS 3,787,454  1/1974  Kerb et al. ............... 260/397.45
3,875,194  4/1975  Laurent et al. ............... 260/397.45

OTHER PUBLICATIONS

"Organic Reactions in Steroid Chemistry," by Fried et al. (1972) pp. 306–313

*Primary Examiner*—Elbert L. Roberts
*Attorney, Agent, or Firm*—Millen & White

[57] ABSTRACT

Compounds of the formula

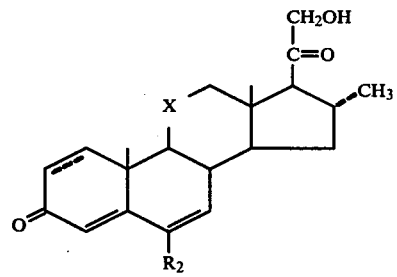

wherein X is β-$CH_2OH$ or CO and $R_2$ is F, Cl or $CH_3$, and their physiologically acceptable 21-esters are useful for the treatment of allergic diseases of the respiratory tract and for the treatment of topical and systemic inflammatory conditions.

5 Claims, No Drawings

NOVEL CORTICOIDS

BACKGROUND OF THE INVENTION

This invention relates to novel pharmacologically active corticoids, to pharmaceutical compositions comprising them and to a process for the preparation thereof.

SUMMARY OF THE INVENTION

In a composition aspect, this invention relates to novel corticoids of general Formula I

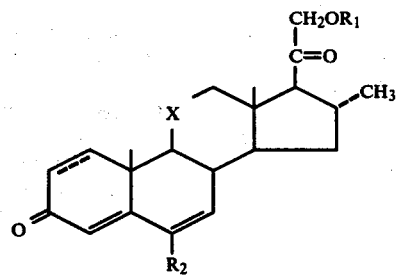

(I)

wherein the bond ≡≡≡ represents a single bond or a double bond, X represents a β-hydroxymethylene group or a carbonyl group, $R_1$ represents a hydrogen atom or the acyl radical of a physiologically acceptable acid, and $R_2$ represents a fluorine atom, a chlorine atom, or a methyl group.

In another composition aspect, this invention relates to pharmaceutical compositions comprising a novel compound of Formula I and in process aspects, this invention relates to methods for making and using the compounds of Formula I.

DETAILED DISCUSSION

Preferred physiologically acceptable $R_1$ acyl groups are the acyl radicals of alkanoic and alkanedioic acids of 1-16, more preferably 2-8, carbon atoms. However, contemplated equivalents of these preferred acyl radicals are the acyl radicals of other physiologically acceptable straight- and branched-chain and saturated and unsaturated aliphatic mono- and dicarboxylic acids, which can be substituted in the usual manner, for example, by one or more hydroxy, amino and halogen atoms, cycloaliphatic, aryl, mixed arylaliphatic, and heterocyclic acids, which can likewise be substituted in the usual manner, aliphatic and aromatic sulfonic acids and inorganic acids, e.g., sulfuric and phosphoric acids. Examples of suitable acyl groups are formyl, acetyl, propionyl, butyryl, pentanoyl, hexanoyl, octanoyl, undecanoyl, dimethylacetyl, trimethylacetyl, diethylacetyl, tert.-butylacetyl, benzoyl, phenacetyl, cyclopentylpropionyl, hydroxyacetyl, monochloroacetyl, dichloroacetyl, trichloroacetyl, dimethylaminoacetyl, trimethylaminoacetyl, diethylaminoacetyl, piperidinoacetyl, nicotinoyl, p-toluenesulfonyloxy, ω-carboxypropionyl, ω-carboxypentanoyl, —$SO_3H$ and —$OPO(OH)_2$.

For the preparation of water-soluble compounds of Formula I, the 21-acyl compounds having a basic nitrogen group in the acyl residue can be converted into the corresponding acid addition salts, e.g., the hydrochlorides, hydrobromides, sulfates, phosphates, oxalates, tartrates or maleates, and the 21-carboxylic acid monoesters and the sulfuric acid and phosphoric acid esters can be converted into the alkali salts thereof, for example, the sodium or potassium salts, or into the ammonium salts thereof.

The process of this invention for the preparation of the novel corticoids is characterized by conventionally (a) hydroxylating a steroid of general Formula II

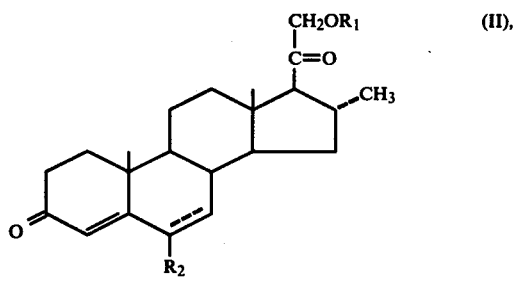

(II), wherein ≡≡≡ $R_1$ and $R_2$ have the above-indicated meanings, in the 11-position; or (b) dehydrogenating a steroid of general Formula III

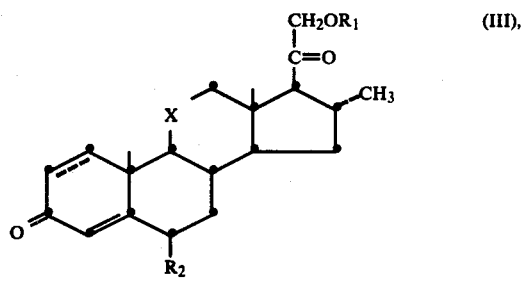

(III), wherein ≡≡≡ X, $R_1$ and $R_2$ have the above-indicated meanings, and optionally dehydrogenating the $\Delta^4$-steroids of general Formula I in the 1,2-position, esterifying a 21-hydroxy group, oxidizing an 11-hydroxy group, and saponifying a 21-acyloxy group.

To conduct the process according to process variation (a), the usual fermentation step is employed with 11α- or 11β-hydroxylating microorganisms. For the 11α-hydroxylation, fungal strains of the genus Aspergillus are preferably used (thus, for example, Aspergillus ochraceus) to serve as the microorganisms. Examples of microorganisms for the 11β-hydroxylation are fungal strains of the genera Curvularia (e.g. Curvularia lunata), Cunninghamella (e.g. Cunninghamella bainieri, Cunninghamella elegans, Cunninghamella echinolata, and Cunninghamella blakesleana), Absidia (e.g. Absidia orchidis and Absidia coerula), Helminthosporium, Rhizoctonia (e.g. Rhizoctonia solani), Verticillium (e.g. Verticillium theobromae), Stachylidium (e.g. Stachylidium bicolor), Pellicularia (e.g. Pellicularia filamentosa), or Colletotrichum (e.g. Colletotrichum pisi). The fermentation with these microorganisms is conducted under the usual conditions. During this reaction, an acyl group in the 21-position is split off in most cases.

The introduction of the $\Delta^6$-double bond according to process variation (b) takes place likewise according to methods known per se. Examples for suitable dehydrogenating agents are chloranil or 2,5-dichloro-5,6-dicyanobenzoquinone.

This dehydrogenation can be conducted so that additionally to the $\Delta^6$-double bond, a $\Delta^1$-double bond is furthermore introduced into the molecule. On the other hand, it is also possible to convert 3-keto-$\Delta^4$-steroids of general Formula III into the 3-alkoxy-$\Delta^{3,5}$-steroids by a conventional process and to dehydrogenate these products with 2,3-dichloro-5,6-dicyanobenzoquinone.

The optionally following step of dehydrogenating the $\Delta^4$-steroids of general Formula I saturated in the 1-position can be accomplished by means of microbiological working methods as well as by means of purely chemical methods. Thus, it is possible, for example, to dehydrogenate the $\Delta^4$-steroids in the 1-position under the usual conditions with bacterial cultures of the genera Bacillus (e.g. Bacillus lentus or Bacillus sphaericus) or Arthrobacter (e.g. Arthrobacter simplex). On the other hand, however, it is also possible to conduct the $\Delta^1$-dehydrogenation by heating the $\Delta^4$-steroids with the oxidizing agents customary for this reaction, for example selenium dioxide or 2,3-dichloro-5,6-dicyanobenzoquinone, in inert solvents.

It is furthermore possible to conventionally brominate the 3-keto-$\Delta^4$-steroids of general Formula I in the 2-position and to split off hydrogen bromide from the thus-obtained bromo steroids.

The oxidation of the 11$\beta$-hydroxy steroids of general Formula I to the corresponding 11-ketones, which can follow as an optional step, takes place according to conventional methods, for example with the aid of chromic acid, N-bromosuccinimide, or N-bromoacetamide.

The optionally following saponification of the 21-esters takes place according to known procedures.

One example in this connection is the saponification of the esters in water or aqueous alcohols in the presence of acidic catalysts, e.g. hydrochloric acid, sulfuric acid, p-toluenesulfonic acid, or of basic catalysts, e.g. potassium bicarbonate, potassium carbonate, sodium hydroxide, or potassium hydroxide.

An esterification of free hydroxy groups in the 21-position, which can follow optionally, likewise takes place with the aid of the conventional working methods. Thus, it is possible, for example, to esterify the hydroxy steroids with acyl chlorides or acyl anhydrides in the presence of acids, e.g. hydrogen chloride, p-toluenesulfonic acid, trifluoroacetic acid, or in the presence of bases, such as potassium carbonate, pyridine, collidine, or p-dimethylaminopyridine. On the other hand, it is possible to esterify the hydroxy compounds in the presence of trifluoroacetic anhydride with carboxylic acids.

From the 21-hydroxy compounds of general Formula I, the alkali sulfates of the 21-monosulfuric acid esters can be prepared in a conventional manner, for example by reacting the 21-hydroxy compounds with sulfur trioxide in pyridine and converting the thus-obtained sulfuric acid ester into the alkali salt by treatment with alkaline bases.

It is furthermore possible to prepare the alkali salts of the 21-monophosphoric acid esters from the 21-hydroxy compounds of general Formula I in a conventional procedure, for example by esterifying the 21-hydroxy compounds, for example, with sulfonic acid chloride in the 21-position; converting the 21-sulfonates with alkali iodide in acetone into the 21-iodo compounds; reacting the iodo compounds with phosphoric acid in the presence of an organic base; and converting the resultant phosphoric acid monoesters with alkali into the dialkali metal salts.

The novel corticoids of general Formula I possess, as mentioned above, a high antiphlogistic activity and are distinguished by a favorable dissociation between the desired, anti-inflammatory effectiveness and undesired thymolytic, catabolic, and mineralocorticoid side effects.

The desired anti-inflammatory effectiveness was determined by means of the conventional adjuvant-edema test:

SPF rats [specific-pathogen free rats] weighing 130 to 150 g. are injected, for producing a center of inflammation, in the right hind paw with 0.1 ml. of a 0.5% Mycobacterium butyricum suspension (obtainable from the U.S. company Difco). Prior to injection, the paw volume of the rats is measured. Twenty-four hours after the injection, the paw volume is measured once again to determine the extent of the edema. Thereafter, various amounts of the test substance are applied to the rats per os. After another 24 hours, the paw volume is once again determined.

From the thus-obtained paw volumes, the edema-inhibitory effect, expressed as a percentage, is calculated in the usual manner. In this test, the compound of this invention, 11$\beta$,21-dihydroxy-6,16$\alpha$-dimethyl-1,4,6-pregnatriene-3,20-dione, at a dose of 7.5 mg./kg. of body weight, shows a 50% edema-inhibitory effect, whereas the commercially available fluocortolone (6$\alpha$-fluoro-11$\beta$,21-dihydroxy-16$\alpha$-methyl-1,4-pregnadiene-3,20-dione), the comparison compound, shows a 50% edema-inhibiting effect at a dose of 10 mg./kg. of body weight.

The undesired side effects were determined by means of the conventional thymolysis test.

To determine the thymolytic effect, SPF rats weighing 70–110 g. are adrenalectomized under ether narcosis. Six animals, respectively, form a test group and over a period of three days a defined amount of test compound is applied orally to the animals. On the fourth day, the animals are sacrificed and the weight of their thymus is determined. The control animals are treated in the same manner but do not receive any test compound. From the thus-obtained thymus weights, the thymolytic effect, expressed in percentages, is calculated in the usual manner.

The comparison substance employed is here again 6$\alpha$-fluoro-11$\beta$,21-dihydroxy-16$\alpha$-methyl-1,4-pregnadiene-3,20-dione which shows a 50% thymolytic effect at a dose of 1.0 mg./kg. of body weight. In contrast thereto, the compound of this invention 11$\beta$,21-dihydroxy-6,16$\alpha$-dimethyl-1,4,6-pregnatriene-3,20-dione causes a 50% thymolysis only at a dose of 3 mg./kg. of body weight.

The fact that the compounds of this invention cause lower systemic side effects was also determined by means of the conventional liver glycogen test.

The novel corticoids are well suitable, together with the excipients customary in galenic pharmacy, for the treatment of, for example:

(a) locally: contact dermatitis, eczemas of a great variety of types, neurodermitis, erythrodermia, first-degree burns, pruritus vulvae et ani, rosacea, erythematodes cutaneus, psoriasis, lichen ruber planus et verrucosus;

(b) orally: acute and chronic polyarthritis, neurodermitis, bronchial asthma, hay fever, and others.

Moreover, the corticoids of this invention are also suitable for the treatment of allergic diseases of the respiratory tract, for example rhinitis or bronchial asthma.

The medicinal specialties are prepared in the usual manner by converting the compounds of this invention together with suitable additives, carriers, and flavor-ameliorating agents, into the desired forms of application, such as tablets, dragees, capsules, solutions, ointments, inhalants, etc.

Especially suitable for oral administration are, in particular, tablets, dragees, and capsules, containing, for example, 0.1–50 mg. of corticoid and 50 mg. to 2 g. of a pharmacologically inert vehicle, e.g. lactose, amylose, talc, gelatin, magnesium stearate, and similar materials, as well as the customary additives. Suitable for topical administration are powders, ointments, aerosols, and similar preparations containing preferably 0.01–2% of the corticoid.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The temperatures in the examples are set forth in degrees Celsius.

EXAMPLE 1

(a) A solution of 24.0 g. of 3β-hydroxy-6,16α-dimethyl-5-pregnen-20-one in 840 ml. of chloroform is combined with 4.8 g. of anhydrous sodium sulfate and 15.6 g. of anhydrous sodium acetate and cooled to +2°. Then, 24 ml. of 40% peracetic acid is added dropwise to the mixture. During this step, another 4.8 g. of anhydrous sodium sulfate and 15.6 g. of anhydrous sodium acetate are added.

The reaction mixture is stirred for one hour at 5° and another hour at 15°, neutralized with 5% aqueous sodium bicarbonate solution, the organic phase is separated, washed with water, dried over sodium sulfate, and concentrated under vacuum. The residue is recrystallized from ethyl acetate, thus obtaining 21.2 g. of 5α,6α-epoxy-3β-hydroxy-6β,16α-dimethylpregnan-20-one, m.p. 185°–188°.

(b) Under agitation and under a nitrogen atmosphere, a sodium ethylate solution produced from 2.1 g. of sodium and 60 ml. of ethanol is added dropwise to a solution of 25.0 g. of 5α,6α-epoxy-3β-hydroxy-6β,16α-dimethylpregnan-20-one in 350 ml. of absolute methylene chloride, whereafter a solution of 25 ml. of oxalic acid diethyl ester in 15 ml. of absolute methylene chloride is also added dropwise to the reaction mixture.

The reaction mixture is heated for 8 hours to 60°, concentrated to dryness under vacuum, the residue extracted under boiling with 700 ml. of hexane and 70 ml. of methylene chloride, and the result is 39 g. of a crystalline crude product.

The crude product is dissolved in 600 ml. of methanol, cooled to −15°, and combined within an hour, under nitrogen and while stirring the reaction mixture, dropwise with a solution of 19.5 g. of iodine in 250 ml. of methanol. The mixture is agitated for 90 minutes at −15°, and then within 40 minutes a solution of 4.3 g. of sodium methylate in 45 ml. of methanol is added dropwise. The mixture is thereafter agitated for another 90 minutes, and then within 2½ hours 140 ml. of water is added dropwise, during which step the reaction mixture is allowed to return to room temperature. The thus-separated product is taken up in a mixture of acetone-ethyl acetate, the aqueous phase is extracted with ethyl acetate, and the combined organic phases are concentrated under vacuum.

The thus-obtained residue is dissolved in 600 ml. of acetone, cooled to 0°, and combined under agitation with 38 ml. of glacial acetic acid and 64 ml. of triethylamine. The mixture is heated for 2 hours under reflux, 350 ml. of acetone is removed by distillation, and the mixture is then combined with 1 liter of water. The aqueous phase is removed by decanting, and the residue is dried under vacuum. The thus-obtained remainder is washed with hexane, dried, and the yield is 22.6 g. of 21-acetoxy-5α,6α-epoxy-3β-hydroxy-6β,16α-dimethylpregnan-20-one, decomposition point 80°–85°.

(c) A glass fermentor having a capacity of 20 liters is charged with 15 liters of a nutrient solution made up of 0.3% yeast extract, 0.5% corn steep liquor, and 0.2% glucose, sterilized by heating for 30 minutes to 120°, and after cooling is inoculated with 250 ml. of a 2 day old shake flask culture of Flavobacterium dehydrogenans (ATCC 13 930). (This shaken culture is prepared by the inoculation of 250 ml. of the same medium with a supernatant broth of a 7 day old agar slant culture.) The subculture is agitated at 220 r.p.m. for 24 hours under aeration (600 liters/hour), and then 1.8 l. of culture is withdrawn therefrom and transferred into a 50-liter fermentor charged with 30 l. of the same medium. The culture is agitated under aeration (15 liters/minute) at 220 r.p.m. for 6 hours at 30°, combined with a sterile-filtered solution of 14 g. of 21-acetoxy-5α,6α-epoxy-3β-hydroxy-6β,16α-dimethylpregnan-20-one in 200 ml. of dimethylformamide, and fermented for another 17 hours under agitation and aeration.

After the fermentation is finished, the culture broth is extracted with methyl isobutyl ketone, the extract is concentrated under vacuum, the residue is washed with hexane and recrystallized from ethyl acetate, thus obtaining 16 g. of 6α,21-dihydroxy-6β,16α-dimethyl-4-pregnene-3,20-dione, m.p. 220°–223°.

(d) 7.7 g. of 6α,21-dihydroxy-6β,16α-dimethyl-4-pregnene-3,20-dione is dissolved in 1.3 l. of absolute benzene, combined with 3.5 g. of p-toluenesulfonic acid, and refluxed for 2 hours; during this step, the thus-formed water is removed by means of a water trap. The mixture is then filtered, the filtrate is washed with 5% aqueous sodium bicarbonate solution and water, and concentrated to dryness under vacuum. The residue is recrystallized from diisopropyl ether, thus obtaining 4.8 g. of 21-hydroxy-6,16α-dimethyl-4,6-pregnadiene-3,20-dione, m.p. 123°–125°.

(e) A 2-liter Erlenmeyer flask containing 100 ml. of a sterile nutrient solution composed of 3% glucose, 1% corn steep liquor, 0.2% sodium nitrate, 0.1% potassium dihydrogen phosphate, 0.2% dipotassium hydrogen phosphate, 0.05% magnesium sulfate, and 0.05% potassium chloride is inoculated with a lyophilized culture of Curvularia lunata NRRL 2380 and shaken for two days at 30° at a frequency of 145 r.p.m.

A glass fermentor with 14.5 l. of the same nutrient medium is inoculated with 0.5 l. of the subculture and incubated under agitation (220 r.p.m.) and aeration (15 liters/minute) for 6 hours at 30°. Then, the culture is combined with a sterile-filtered solution of 3 g. of 21-hydroxy-6,16α-dimethyl-4,6-pregnadiene-3,20-dione in 150 ml. of dimethylformamide, and fermented under agitation and aeration for another 136 hours.

Then, the culture broth is extracted with methyl isobutyl ketone, the extract is concentrated under vacuum, the residue is washed with hexane and purified by chromatography over a silica gel column. The thus-obtained product is recrystallized from ethyl acetate, yielding 841 mg. of 11β,21-dihydroxy-6,16α-dimethyl-4,6-pregnadiene-3,20-dione, m.p. 242°–244°.

EXAMPLE 2

A 2-liter Erlenmeyer flask containing 200 ml. of a sterile nutrient medium consisting of
1.2% corn steep liquor and 1.5% peptone is inoculated with a lyophilized culture of Bacillus lentus (ATCC 13 805) and shaken for 2 days at 30° at 145 r.p.m.

A 20-liter glass fermentor with 10 l. of a sterile nutrient solution containing 0.1% yeast extract, 0.5% corn steep liquor, and 0.2% glucose is inoculated with the subculture and agitated for one day under aeration (10 liters/minute) at 30° at 220 r.p.m.

One liter of the germination culture is transferred in 7 l. of the same nutrient solution into a fermentor of equal size. After a germination period of 6 hours under agitation and aeration, a sterile-filtered solution of 800 mg. of 11β,21-dihydroxy-6,16α-dimethyl-4,6-pregnadiene-3,20-dione in 50 ml. of dimethylformamide is added and the mixture fermented for another 20 hours.

The reaction mixture is worked up as described in Example 1(e), the thus-obtained crude product is recrystallized from diisopropyl ether-methylene chloride, and the product is 400 mg. of 11β,21-dihydroxy-6,16α-dimethyl-1,4,6-pregnatriene-3,20-dione, m.p. 140°–143°.

EXAMPLE 3

80 mg. of 11β,21-dihydroxy-6,16α-dimethyl-1,4,6-pregnatriene-3,20-dione is combined with 2.5 ml. of absolute pyridine and 0.2 ml. of acetic anhydride and stored at room temperature for 4 hours. The reaction mixture is then poured into 50 ml. of 1 N sulfuric acid, extracted with chloroform, the chloroform phase is washed, concentrated under vacuum, and the yield is 65 mg. of 21-acetoxy-11β-hydroxy-6,16α-dimethyl-1,4,6-pregnatriene-3,20-dione.

EXAMPLE 4

75 mg. of 11β,21-dihydroxy-6,16α-dimethyl-1,4,6-pregnatriene-3,20-dione is combined with 2.5 ml. of absolute pyridine and 0.2 ml. of valeric acid anhydride and shaken for 4 hours at room temperature. The reaction mixture is worked up as described in Example 3, thus obtaining 60 mg. of 11β-hydroxy-6,16α-dimethyl-21-valeryloxy-1,4,6-pregnatriene-3,20-dione.

EXAMPLE 5

80 mg. of 11β,21-dihydroxy-6,16α-dimethyl-1,4,6-pregnatriene-3,20-dione is combined with 2.5 ml. of absolute pyridine and 0.25 g. of succinic anhydride and shaken for 4 hours at room temperature.

The reaction mixture is worked up as described in Example 3, thus obtaining 60 mg. of 21-hemisuccinyloxy-11β-hydroxy-6,16α-dimethyl-1,4,6-pregnatriene-3,20-dione.

EXAMPLE 6

Under the conditions of Example 1(e), 10 l. of a culture of Cunninghamella elegans (ATCC 9245) are incubated, and after an incubating phase of 12 hours, 1.9 g. of 21-hydroxy-6,16α-dimethyl-4,6-pregnadiene-3,20-dione, dissolved in 60 ml. of dimethylformamide, is added and the mixture fermented for another 62 hours.

The culture broth is worked up as described in Example 1(e), thus obtaining 270 mg. of 11β,21-dihydroxy-6,16α-dimethyl-4,6-pregnadiene-3,20-dione.

EXAMPLE 7

(a) A 2-liter Erlenmeyer flask containing 500 ml. of a sterile nutrient solution containing 1% corn steep liquor, 1.25% soybean meal, and 0.005% soybean oil is inoculated with a supernatant broth of a 10 day old culture of Aspergillus ochraceus ATCC 1008, grown on corn kernels, and shaken for 72 hours at 30° at 165 r.p.m.

With 250 ml. of this germination culture, 15 l. of the same nutrient solution is inoculated in a 20-liter glass fermentor, and the germination is carried out under agitation (220 r.p.m.) and aeration (15 liters/minute) for 24 hours at 30°. 900 ml. of the subculture are transferred into a fermentor of equal size charged with 14 l. of the same nutrient solution and stirred under aeration at 30° for 12 hours. The culture is then combined with a sterile-filtered solution of 2.75 g. of 21-hydroxy-6,16α-dimethyl-4,6-pregnadiene-3,20-dione in 110 ml. of dimethylformamide and the mixture is fermented for another 27 hours.

The culture broth is worked up as described in Example 1(e), thus obtaining 2.1 g. of 11α,21-dihydroxy-6,16α-dimethyl-4,6-pregnadiene-3,20-dione, m.p. 192°–194° (from ethyl acetate).

(b) Under the conditions of Example 2, 3 g. of 11α,21-dihydroxy-6,16α-dimethyl-4,6-pregnadiene-3,20-dione is reacted in 15 l. of a Bacillus lentus (ATCC 13805) culture; the reaction mixture is worked up, and the result is 1.2 g. of 11α,21-dihydroxy-6,16α-dimethyl-1,4,6-pregnatriene-3,20-dione, m.p. 171°–172° (from ethyl acetate).

(c) 4 g. of 11α,21-dihydroxy-6,16α-dimethyl-1,4,6-pregnatriene-3,20-dione is dissolved in 40 ml. of dimethylformamide, combined with 400 mg. of lead diacetate and 8.3 ml. of acetic anhydride, and agitated for 90 minutes at room temperature.

The reaction mixture is then poured into 300 ml. of 10% sodium acetate solution and agitated for one hour. The precipitate is vacuum-filtered, washed with water, dried under vacuum, and recrystallized from ethyl acetate-diisopropyl ether, thus obtaining 3.74 g. of 21-acetoxy-11α-hydroxy-6,16α-dimethyl-1,4,6-pregnatriene-3,20-dione, m.p. 166°–167°.

(d) Under agitation a solution of 533 mg. of chromium(VI) oxide in 25 ml. of 90% acetic acid is added dropwise within 2 hours to a solution of 2 g. of 21-acetoxy-11α-hydroxy-6,16α-dimethyl-1,4,6-pregnatriene-3,20-dione in 40 ml. of 90% acetic acid. The reaction mixture is agitated for another 4½ hours and then poured into 800 ml. of 8% sodium bicarbonate solution; the precipitate is vacuum-filtered, washed with water, and dried under vacuum.

The aqueous phase is extracted with methylene chloride, the methylene chloride phase is concentrated, and another 330 mg. of crude product is thus obtained.

The combined crude products are recrystallized from diisopropyl ether-hexane, thus obtaining 1.42 g. of 21-acetoxy-6,16α-dimethyl-1,4,6-pregnatriene-3,11,20-trione, m.p. 122°–123°.

(e) 500 mg. of 21-acetoxy-6,16α-dimethyl-1,4,6-pregnatriene-3,11,20-trione is combined under nitrogen with a solution of 132 mg. of sodium methylate in 35 ml. of methanol. After 5 minutes, the reaction mixture is combined with 0.13 ml. of water, neutralized with acetic acid, and concentrated under vacuum. The residue is diluted with water, extracted with ethyl acetate, the ethyl acetate phase is concentrated under vacuum, and the residue is recrystallized from diisopropyl ether-acetone, thus obtaining 155 mg. of 21-hydroxy-6,16α-dimethyl-1,4,6-pregnatriene-3,11,20-trione, m.p. 162°–164°.

EXAMPLE 8

(a) A solution of 110 g. of 21-acetoxy-16α-methyl-4-pregnene-3,20-dione in 550 ml. of ethanol and 330 ml. of 1,2-dimethoxyethane is heated to 40° and combined with a solution of 9 g. of p-toluenesulfonic acid in 200 ml. of 1,2-dimethoxyethane, as well as with 116 g. of the triethyl ester of orthoacetic acid. The temperature is maintained at 40°. After 20 minutes, another 2.5 g. of p-toluenesulfonic acid is added. The mixture is maintained at 40° for 30 minutes, then cooled to 10°, and combined with 12 ml. of pyridine as well as 2.7 g. of sodium acetate in 50 ml. of water. The solution is poured into 3,000 ml. of ice water and the mixture extracted with dichloromethane. The organic phase is washed with water, dried over sodium sulfate, filtered, and concentrated under vacuum. The residue of 130 g. is dissolved under ice cooling in 800 ml. of acetone. The solution is combined with 536 ml. of water, 17 ml. of pyridine, and 94 g. of sodium acetate. Under agitation, 106 g. of N-chlorosuccinimide and 143 ml. of acetic acid is added thereto and the mixture is stirred for 30 minutes at 5°. Subsequently, a solution of 37 g. of sodium bisulfite in 144 ml. of water is added thereto, and the mixture is once again agitated for 20 minutes. The reaction solution is stirred into 15 liters of ice water, the thus-obtained precipitate is filtered off, washed with water, and dried in the air. The crude product of 122 g. is chromatographed on silica gel. With 10-22% acetone-dichloromethane, after recrystallization from acetone-dichloromethane, 62.8 g. of 21-acetoxy-6α-chloro-11β-hydroxy-16α-methyl-4-pregnene-3,20-dione is obtained, m.p. 209° $[\alpha]_D^{25} = +176°$ (pyridine). UV: $\epsilon_{237} = 14,100$ (methanol).

(b) 5.0 g. of 21-acetoxy-6α-chloro-11β-hydroxy-16α-methyl-4-pregnene-3,20-dione is combined with 45 ml. of ethylene glycol dimethyl ether, as well as 100 mg. of p-toluenesulfonic acid, and the mixture is stirred for 15 minutes at 10°–15°. Then, 18 ml. of ethanol is added thereto, and the mixture is combined with 3.1 ml. of triethyl ester of orthoacetic acid, and again agitated for 40 minutes at 20°–25°. The mixture is cooled to 10°, and a solution of 392 mg. of sodium acetate in 19 ml. of water is added dropwise thereto. The reaction solution is then brought to room temperature, combined with 7 ml. of dichloromethane as well as 30 ml. of water, and agitated for 20 minutes at 10°. The mixture is extracted several times with dichloromethane. The combined organic phases are washed with dilute sodium acetate solution. The product is concentrated under vacuum to 5 ml. and then 0.1 ml. of pyridine is added. The solution is diluted with 20 ml. of dioxane, combined with 2 ml. of water, as well as with 2.5 g. of dichlorodicyanobenzoquinone, and agitated for 80 minutes under ice cooling. One gram of sodium bisulfite, dissolved in 5 ml. of water, is added thereto and the mixture is concentrated under vacuum to 10 ml. and stirred into ice water. The mixture is agitated for one hour, the thus-obtained precipitate is filtered and washed with water. The moist residue is combined with 50 ml. of dichloromethane and stirred for 40 minutes at room temperature. This process is repeated once again. The dichloromethane solutions are washed with water, dried over sodium sulfate, filtered, and concentrated under vacuum. The crude product, 6.2 g. of foam, is chromatographed on silica gel. With 55-67% ethyl acetate-hexane, 1.34 g. of 21-acetoxy-6-chloro-11β-hydroxy-16α-methyl-4,6-pregnadiene-3,20-dione is obtained after recrystallization from acetonediisopropyl ether; m.p. 171° $[\alpha]_D^{25} = +176°$ (methanol). UV: $\epsilon_{285} = 17,800$ (methanol).

EXAMPLE 9

A solution of 2.95 g. of 21-acetoxy-6-chloro-11β-hydroxy-16α-methyl-4,6-pregnadiene-3,20-dione in 80 ml. of methanol is combined with 800 mg. of potassium carbonate and stirred for 5 minutes at room temperature under argon. After adding 5 ml. of acetic acid and 5 ml. of water, the reaction solution is completely evaporated under vacuum. The residue is chromatographed on silica gel. With 42-50% acetone-hexane and after recrystallization from acetone-diisopropyl ether, 1.55 g. of 6-chloro-11β,21-dihydroxy-16α-methyl-4,6-pregnadiene-3,20-dione is obtained, m.p. 229° $[\alpha]_D^{25} = +175°$ (methanol). UV: $\epsilon_{285} = 19,850$ (methanol).

EXAMPLE 10

A solution of 10.45 g. of 21-acetoxy-6-chloro-11β-hydroxy-16α-methyl-4,6-pregnadiene-3,20-dione in 80 ml. of tetrahydrofuran is combined with 6.5 g. of pyridinium hydrobromide perbromide in 26 ml. of tetrahydrofuran and agitated for 20 minutes at 25°. Subsequently, 0.6 ml. of acetone is added thereto and the mixture is filtered. The filtrate is concentrated under vacuum to a volume of 10 ml., and combined with 80 ml. of dimethylformamide, 4.5 g. of lithium carbonate, as well as 1.62 g. of lithium bromide. The mixture is heated for 2.5 hours to 105° and concentrated under vacuum at 60° to a volume of 40 ml. The mixture is combined with 10 ml. of acetic acid and 14 ml. of water and stirred into 350 ml. of ice water. The thus-obtained precipitate is filtered off, washed with water, and dried in the air. The crude product, 9.4 g., is chromatographed on silica gel. With 40% ethyl acetate-hexane and after recrystallization from acetone-diisopropyl ether, 1.81 g. of 21-acetoxy-6-chloro-11β-hydroxy-16α-methyl-1,4,6-pregnatriene-3,20-dione is obtained, m.p. 192° $[\alpha]_D^{25} = +136°$ (pyridine). UV: $\epsilon_{228} = 11,100$, $\epsilon_{256} = 10,500$, $\epsilon_{299} = 9,800$ (methanol).

EXAMPLE 11

A hydrogen chloride stream is introduced into a solution of 1.0 g. of 21-acetoxy-6α-chloro-11β-hydroxy-16α-methyl-4-pregnene-3,20-dione in 100 ml. of dioxane for 30 minutes at 25° after adding 1.5 g. of dichlorodicyanobenzoquinone. The solution is then heated for 15 hours to 120°. After cooling, the solution is filtered, the filter cake washed with dichloromethane, and the filtrate evaporated under vacuum. The residue of the evaporation is chromatographed on silica gel. With 32-40% acetone-hexane, after recrystallization from acetone-diisopropyl ether, 380 mg. of 21-acetoxy-6-chloro-11β-hydroxy-16α-methyl-1,4,6-pregnatriene-3,20-dione is obtained.

EXAMPLE 12

A solution of 7.8 g. of 21-acetoxy-6-chloro-11β-hydroxy-16α-methyl-1,4,6-pregnatriene-3,20-dione in 220 ml. of methanol is combined with 2.3 g. of potassium carbonate and agitated under argon for 5 minutes at room temperature. The solution is combined with 5 ml. of acetic acid and 5 ml. of water and concentrated to half its volume under vacuum. The mixture is then washed with water, extracted with methylene chloride, the organic phase is dried over sodium sulfate, and the solvent is evaporated. The residue is recrystallized from acetone-diisopropyl ether. Yield: 2.53 g. of 6-chloro-11β,21-dihydroxy-16α-methyl-1,4,6-pregnatriene-3,20-dione, m.p. 215°. UV: $\epsilon_{227}=12,000$, $\epsilon_{256}=10,500$, $\epsilon_{299}=10,200$ (methanol).

EXAMPLE 13

A solution of 750 mg. of 6-chloro-11β,21-dihydroxy-16α-methyl-1,4,6-pregnatriene-3,20-dione in 5 ml. of pyridine is combined with 2.5 ml. of butyric acid anhydride and agitated for 15 hours at room temperature. After adding 1 ml. of water, the solution is heated for 15 minutes on a steam bath and then poured into ice water. The thus-precipitated product is filtered off, washed with water, and dissolved in dichloromethane. The solution is dried over sodium sulfate, filtered, and concentrated under vacuum. The residue is chromatographed on 15 silica gel plates, 20 cm.×60 cm., layer thickness 1 mm. The eluent is hexane-ethyl acetate (1:1). After recrystallization from acetone-diisopropyl ether, 417 mg. of 21-butyryloxy-6-chloro-11β-hydroxy-16α-methyl-1,4,6-pregnatriene-3,20-dione, m.p. 203° $[\alpha]_D^{25}=+81°$ (chloroform). UV: $\epsilon_{228}=10,900$, $\epsilon_{255}=10,400$, $\epsilon_{299}=9,500$ (methanol).

EXAMPLE 14

750 mg. of 6-chloro-11β,21-dihydroxy-16α-methyl-1,4,6-pregnatriene-3,20-dione is dissolved in a mixture of 5 ml. of pyridine and 2.5 ml. of valeric acid anhydride. The solution is maintained at room temperature for 15 hours. After adding 1 ml. of water, the mixture is heated for 30 minutes on a steam bath and then stirred into ice water. After 3 hours, the thus-precipitated product is filtered off, washed with water, and dissolved in dichloromethane. The solution is dried over sodium sulfate, filtered, and concentrated under vacuum. The residue is chromatographed on 20 silica gel plates, 20 cm.×60 cm., layer thickness 1 mm. The eluent is hexane-ethyl acetate (1:1). After recrystallization from acetone-diisopropyl ether, 370 mg. of 6-chloro-11β-hydroxy-16α-methyl-21-valeryloxy-1,4,6-pregnatriene-3,20-dione, m.p. 193° $[\alpha]_D^{25}=+81°$ (chloroform). UV: $\epsilon_{229}=11,000$, $\epsilon_{255}=10,600$, $\epsilon_{299}=9,500$ (methanol).

EXAMPLE 15

20 g. of 21-acetoxy-6α-fluoro-11β-hydroxy-16α-methyl-4-pregnene-3,20-dione is reacted according to the procedure set forth in Example 8(b), thus obtaining 18 g. of a crude product which is chromatographed on silica gel. With 31–37% ethyl acetate-dichloromethane, 7.8 g. of 21-acetoxy-6-fluoro-11β-hydroxy-16α-methyl-4,6-pregnadiene-3,20-dione is eluted, m.p. 177° (from acetone-diisopropyl ether). $[\alpha]_D^{25}=+124°$ (chloroform). UV: $\epsilon_{283}=18,500$ (methanol).

EXAMPLE 16

400 mg. of 21-acetoxy-6-fluoro-11β-hydroxy-16α-methyl-4,6-pregnadiene-3,20-dione is saponified under the conditions described in Example 12. The crude product is crystallized from acetone-diisopropyl ether. Yield: 187 mg. of 6-fluoro-11β,21-dihydroxy-16α-methyl-4,6-pregnadiene-3,20-dione, m.p. 244° $[\alpha]_D^{25}=+112°$ (chloroform). UV: $\epsilon_{285}=19,900$ (methanol).

EXAMPLE 17

1.4 g. of 21-acetoxy-6-fluoro-11β-hydroxy-16α-methyl-4,6-pregnadiene-3,20-dione is converted according to Example 10 into 21-acetoxy-6-fluoro-11β-hydroxy-16α-methyl-1,4,6-pregnatriene-3,20-dione. Yield: 198 mg., m.p. 197°, recrystallized from acetone-diisopropyl ether. $[\alpha]_D^{25}=+29°$ (chloroform). UV: $\epsilon_{225}=11,500$, $\epsilon_{257}=10,900$, $\epsilon_{298}=11,200$ (methanol).

EXAMPLE 18

2.0 g. of acetoxy-6α-fluoro-11β-hydroxy-16α-methyl-4-pregnene-3,20-dione is converted according to the method described in Example 11 into 21-acetoxy-6-fluoro-11β-hydroxy-16α-methyl-1,4,6-pregnatriene-3,20-dione; yield: 810 mg.

EXAMPLE 19

700 mg. of 21-acetoxy-6-fluoro-11β-hydroxy-16α-methyl-1,4,6-pregnatriene-3,20-dione is saponified analogously to Example 12. Yield: 372 mg. 6-fluoro-11β,21-dihydroxy-16α-methyl-1,4,6-pregnatriene-3,20-dione, m.p. 241°, recrystallized from acetone-diisopropyl ether. $[\alpha]_D^{25}=+72°$ (pyridine). UV: $\epsilon_{226}=11,000$, $\epsilon_{254}=10,800$, $\epsilon_{299}=9,600$ (methanol).

EXAMPLE 20

750 mg. of 6-fluoro-11β,21-dihydroxy-16α-methyl-1,4,6-pregnatriene-3,20-dione is converted as described in Example 13 into 21-butyryloxy-6-fluoro-11β-hydroxy-16α-methyl-1,4,6-pregnatriene-3,20-dione. Yield: 502 mg., recrystallized from acetone-diisopropyl ether, m.p. 177° $[\alpha]_D^{25}=+34°$ (chloroform). UV: $\epsilon_{228}=12,300$, $\epsilon_{259}=11,000$, $\epsilon_{301}=11,000$ (methanol).

EXAMPLE 21

750 mg. of 6-fluoro-11β,21-dihydroxy-16α-methyl-1,4,6-pregnatriene-3,20-dione is converted, as described in Example 14, into 6-fluoro-11β-hydroxy-16α-methyl-21-valeryloxy-1,4,6-pregnatriene-3,20-dione and recrystallized from acetone-diisopropyl ether. Yield: 584 mg., m.p. 187° $[\alpha]_D^{25}=+36°$ (chloroform). UV: $\epsilon_{225}=11,100$, $\epsilon_{256}=10,600$, $\epsilon_{299}=10,500$ (methanol).

EXAMPLE 22

A solution of 2.0 g. of 6-fluoro-11β,21-dihydroxy-16α-methyl-1,4,6-pregnatriene-3,20-dione in 10 ml. of pyridine is heated after the addition of 1 g. of succinic anhydride for 2 hours to 120° C. The reaction solution is poured into ice water which contains sulfuric acid, the thus-precipitated product is filtered off and dissolved in ethyl acetate. The solution is dried over sodium sulfate and concentrated under vacuum. The remaining residue is chromatographed on silica gel. The product is eluted with ethyl acetate and recrystallized from ethyl acetate-diisopropyl ether, thus obtaining 1.03 g. of 6-fluoro-11β,21-dihydroxy-16α-methyl-1,4,6-pregnadiene-3,20-dione 21-hydrogen succinate. If the reaction is conducted with the use of the corresponding 6-chlorine derivative, then 6-chloro-11β,21-dihydroxy-16α-methyl-1,4,6-pregnatriene-3,20-dione 21-hydrogen succinate is obtained.

EXAMPLE 23

500 mg. of 6-fluoro-11β,21-dihydroxy-16α-methyl-1,4,6-pregnatriene-3,20-dione 21-hydrogen succinate is converted in 20 ml. of methanol with 0.1 N sodium methylate solution into the sodium salt. The salt is precipitated by adding 300 ml. of ether, vacuum-filtered, washed with ether, and dried under vacuum at 50°, thus obtaining 483 mg. of sodium 6-fluoro-11β,21-dihydroxy-16α-methyl-1,4,6-pregnatriene-3,20-dione 21-succinate. Analogously, sodium 6-chloro-11β,21-dihydroxy-16α-methyl-1,4,6-pregnatriene-3,20-dione 21-succinate is obtained.

EXAMPLE 24

A 2-liter Erlenmeyer flask containing 500 ml. of a nutrient solution of 1% corn steep liquor, 1% soybean meal, and 0.005% soybean oil, adjusted to pH 6.2, sterilized for 30 minutes at 120° in an autoclave, is inoculated with a lyophilized culture of Curvularia lunata (NRRL 2380) and shaken for 72 hours at 30° on a rotary shaker with a shaking frequency of 145 r.p.m. This subculture serves for the inoculation of a 20-liter fermentor containing 14 l. of a medium made up of 1% corn steep liquor, 0.5% glucose, and 0.005% soybean oil, adjusted to pH 6.2, sterilized at 121° C. and under 1.1 atmospheres gauge. While adding "Silicon SH" as the defrother, the mixture is germinated at 29° under aeration (10 liters/minute), a pressure of 0.7 atmosphere gauge, and agitation at 220 r.p.m. for 24 hours. One liter of the culture broth is transferred under sterile conditions into 14 l. of a medium sterilized as above, of 1% corn steep liquor, 1.25% soybean meal, and 0.005% soybean oil, and germinated under the same conditions. After 12 hours, a solution of 3 g. of 21-acetoxy-6-chloro-16α-methyl-4,6-pregnadiene-3,20-dione in 150 ml. of dimethylformamide is added and the mixture is further stirred and aerated.

The progression of the conversion step is observed by analyzing the methyl isobutyl ketone extracts of fermentor samples by thin-layer chromatography, thus registering a decrease in the starting material. After complete conversion has taken place (about 30 hours), the content of the fermentor is extracted twice with respectively 10 l. of methyl isobutyl ketone, and the extract is evaporated under vacuum at a bath temperature of 50°. The residue is taken up in methanol, the undissolved silicone oil is separated, and the solution is once again concentrated to dryness under vacuum. To separate by-products, the oily residue is chromatographed by means of the linear elution gradient methylene chloride-acetone over a silica gel column, and then recrystallized from acetone-hexane, thus obtaining 970 mg. of 6-chloro-11β,21-dihydroxy-16α-methyl-4,6-pregnadiene-3,20-dione, m.p. 225°.

EXAMPLE 25

A 2-liter Erlenmeyer flask containing 500 ml. of a nutrient solution of 1.5% peptone, 1.2% corn steep liquor, and 0.2% MgSO$_4$, adjusted to pH 6.5, sterilized for 30 minutes at 120° in an autoclave, is inoculated with a lyophilized culture of Bacillus sphaericus (ATCC 7055) and shaken for 24 hours at 30° on a rotary shaker. With this subculture, a 20-liter fermentor is inoculated, which is filled with 14 l. of a liquid nutrient medium, sterilized at 121° and 1.1 atmospheres gauge and consisting of 0.2% yeast extract, 1% corn steep liquor, and 0.1% glucose, adjusted to pH 7.0. After the addition of "Silicon SH" as the defrother, the mixture is now germinated at 29° under aeration and agitation. After a germination phase of 6 hours, the substrate is added in the form of a solution of 3 g. of 6-chloro-11β,21-dihydroxy-16α-methyl-4,6-pregnadiene-3,20-dione in 150 ml. of dimethylformamide.

After a contact period of 42 hours, the fermentor content is extracted twice with respectively 10 l. of methyl isobutyl ketone, and the extract is evaporated under vacuum. The residue is washed with hexane to remove the silicone oil and then chromatographed over a silica gel column (gradient methylene chloride-methylene chloride/acetone 8+2) for purifying purposes. After crystallization from acetone/hexane, the pure 6-chloro-11β,21-dihydroxy-16α-methyl-1,4,6-pregnatriene-3,20-dione (1.4 g.) melts at 216°.

EXAMPLE 26

Under the conditions of Example 24, 3 g. of 21-acetoxy-6-fluoro-16α-methyl-4,6-pregnadiene-3,20-dione is converted with the aid of Curvularia lunata into 840 mg. of 6-fluoro-11β,21-dihydroxy-16α-methyl-4,6-pregnadiene-3,20-dione, m.p. 239°.

EXAMPLE 27

Under the conditions of Example 25, 3 g. of 6-fluoro-11β,21-dihydroxy-16α-methyl-4,6-pregnadiene-3,20-dione is dehydrogenated by means of Bacillus sphaericus to 1.7 g. of 6-fluoro-11β,21-dihydroxy-16α-methyl-1,4,6-pregnatriene-3,20-dione, m.p. 240°.

Following the procedures of Examples 8 to 25, the 11-keto corticoids otherwise corresponding to the 11β-hydroxy products of these examples can be produced employing 11-keto starting compounds corresponding to the 11-hydroxy steroids employed as starting materials therein.

EXAMPLE 28

Composition for a tablet:

0.250 mg. 11β,21-Dihydroxy-6,16α-dimethyl-1,4,6-pregnatriene-3,20-dione 36.000 mg. lactose DAB 6

75.780 mg. corn starch USP XVI 0.500 mg. sodium lauryl sulfate (Texapon K 12) "Dehydag", USP XVI 1.400 mg. gelatin, white DAB 6

6.000 mg. talcum DAB 6

0.024 mg. Nipagin M (p-oxybenzoic acid methyl ester) DAB 6, 3. supplement 0.011 mg. Nipasol M (p-oxybenzoic acid propyl ester) DAB 6, 3. supplement 0.035 mg Pistachio green dye "Dragoco"

EXAMPLE 29

Preparation of inhalation agent:

1.000 of micronized 11β,21-dihydroxy-6,16α-dimethyl-1,4,6-pregnatriene-3,20-dione (median particle size - less than 7μ) and 39.000 g. of ground lactose were mixed. Then 40 mg. of this mixture was filled into hard gelatin capsules.

The inhalation agent can, after opening of the capsule, be applied in a manner such as usually employed for treatment of a asthma.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

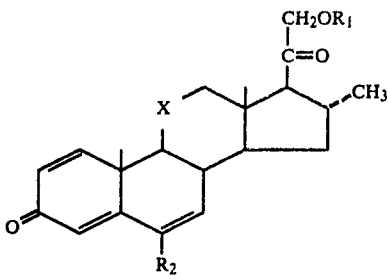

X is carbonyl; $R_1$ is a hydrogen atom or the acyl radical of an alkanoic or alkanedioic acid of up to 16 carbon atoms, and $R_2$ is fluorine, chlorine or methyl.

2. 21-Acetoxy-6,16α-dimethyl-1,4,6-pregnatriene-3,11,20-trione, a compound of claim 1.

3. 21-Hydroxy-6,16α-dimethyl-1,4,6-pregnatriene-3,11,20-trione, a compound of claim 1.

4. A pharmaceutical composition comprising an anti-inflammatorily effective amount of a compound of claim 1 in admixture with a pharmaceutical carrier.

5. A method of treatment of inflammatory conditions in mammals which comprises administering to the afflicted mammal an anti-inflammatorily effective amount of a compound of claim 1.

* * * * *